United States Patent [19]
Jordan et al.

[11] Patent Number: 5,998,643
[45] Date of Patent: Dec. 7, 1999

[54] METALLOCENE SYNTHESIS

[75] Inventors: Richard F. Jordan, Iowa City, Iowa; Bakthavachalam Thiyagarajan, Baton Rouge, La.; Xingwang Zhang, Iowa City, Iowa

[73] Assignee: University of Iowa Research Foundation, Iowa City, Iowa

[21] Appl. No.: 09/232,513

[22] Filed: Jan. 15, 1999

[51] Int. Cl.$^6$ .............................. C07F 17/00; C07F 7/00
[52] U.S. Cl. ................... 556/11; 556/1; 556/20; 556/27; 556/43; 556/53; 502/103; 502/117; 534/15; 526/160; 526/943
[58] Field of Search ................... 556/1, 20, 11, 556/43, 53, 27; 534/15; 502/103, 117; 526/160, 943

[56] References Cited

U.S. PATENT DOCUMENTS

| | | | |
|---|---|---|---|
| 5,495,035 | 2/1996 | Jordan et al. | 556/1 |
| 5,597,935 | 1/1997 | Jordan et al. | 556/11 |
| 5,892,081 | 4/1999 | Silring et al. | 556/28 |

*Primary Examiner*—Porfirio Nazario-Gonzalez
*Attorney, Agent, or Firm*—Zarley, McKee, Thomte, Voorhees & Sease

[57] ABSTRACT

The process of preparing ansa-metallocene complexes in high yield by reacting a metal leaving group complex with an aluminum ansa-bis-cyclopentadienyl compound.

39 Claims, No Drawings

METALLOCENE SYNTHESIS

BACKGROUND OF THE INVENTION

This invention relates to the field, now well established, of use of ansa-metallocenes as catalysts. They are particularly useful as catalysts for the polymerization of ethylene and alpha olefins such as propylene.

Conventional heterogeneous catalysts such as Ziegler-Natta systems have a variety of active sites, only some of which are stereo-specific. Obtaining a polymer with specific properties can involve a considerable amount of trial and error in order to find the best combination of catalyst, co-catalyst and stereo-regulator. In contrast, however, the active polymerization site in a metallocene catalyst is well defined, and can be modified in a straightforward manner via modification of the cyclopentadienyl ligands, enabling the structure of the polymer to be controlled with far greater precision.

A simple metallocene catalyst for polymerizing ethylene is $(C_5H_5)_2ZrCl_2$ which consists of a zirconium atom bound to two chlorine atoms and two cyclopentadienyl rings, and which is activated by co-catalysts such as methylaluminoxane (MAO). During the 1980's, ansa or bridged metallocenes, in which the cyclopentadienyl rings are linked by a chemical bridge, were found to be particularly useful for the polymerization of olefins. In particular, ansa-metallocene complexes, when used in combination with a co-catalyst such as methylaluminoxane (MAO), polymerize propylene to highly isotactic polypropylene, highly syndiotactic polypropylene, or atactic polypropylene, depending on the structure of the ansa-metallocene used.

As is well known, isotactic polymers have each pendant group attached to the backbone in the same orientation, whereas in syndiotactic polymers, these groups alternate in their orientations and atactic polymers have a random arrangement of the groups along the backbone. Since the stereochemistry of the polymer has a great effect on its properties, it is desirable to control this feature. Chiral, $C_2$-symmetric ansa-metallocenes produce isotactic polypropylene.

While the greatest area of potential use for ansa-metallocene catalysts currently is for polymerization of olefins, such as ethylene and propylene, they also have significant uses as catalysts or catalyst precursors for other reactions where stereo-selectivity is important.

The utility of ansa-metallocene complexes as catalysts for olefin polymerization and other reactions has created a high demand for a practical synthesis of ansa-metallocene compounds.

In spite of this demand, current procedures for the synthesis of Group 4 (Ti,Zr,Hf) ansa-metallocenes based on the use of ansa-bis-cyclopentadienyl dianion reagents are hampered by low yields and tedious isomer separation and purification steps. Some of these problems have been discussed in Ellis, W. W.; Hollis, T. K.; Odenkirk, W., Whelan, J.; Ostrander, R.; Rheingold, A. L.; Bosnich, B. *Organometallics* 1993, 12, 4391. In particular, the synthesis of chiral $C_2$ symmetric ansa-metallocenes typically produces mixtures of desired rac (racemic) and undesired meso isomers. A typical synthesis of an ansa-metallocene complex is shown in equation 1 below:

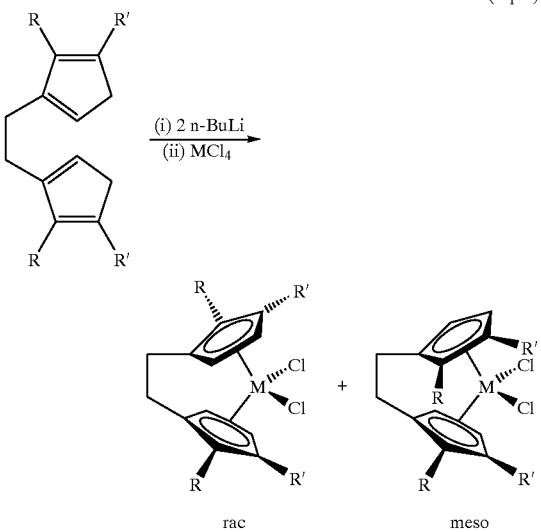

(Eq. 1)

This equation is typical of the process as shown in the art. See for example Spaleck, W.; Kuber, F., Winter, A.; Rohrman, J.; Bachmann, B.; Antberg, M.; Dolle, V.; Paulus, E. F. *Organometallics* 1994, 13, 954. Stehling, U.; Diebold, J.; Kirsten, R.; Roll, W.; Brintzinger, H. H.; Jungling, S.; Mulhaupt, R.; Langhauser, F. *Organometallics* 1994, 13, 964. Halterman, R. L. *Chem. Rev.* 1992, 92, 965. See also, for example, U.S. Pat. No. 5,145,819, U.S. Pat. No. 5,268,495, and EPA 0-530-908-A1.

By way of further example, an important chiral Group 4 ansa-metallocene is rac-$(EBI)ZrCl_2$ (EBI=ethylene-1,2-bis (1-indenyl) which is currently prepared from $ZrCl_4$ and the dianion of the EBI ligand (Halterman, R. L. *Chem. Rev.* 1992, 92, 965). Brintzinger (Wild, F. R. W. P.; Wasiucionek, M.; Huttner, G., Brintzinger, H. H. *J. Organomet. Chem.* 1985, 288, 63) and Collins (Collins, S.; Kuntz, B. A.; Hong, Y. *J. Org. Chem.* 1989, 54, 4154; Collins, S.; Kuntz, B. A.; Taylor, N. J.; Ward, D. G. *J. Organomet. Chem.* 1988, 342, 21) used $(EBI)Li_2$ and reported low, variable yields (20–50%) of rac-$(EBI)ZrCl_2$. Buchwald employed $(EBI)K_2$ and obtained $(EBI)ZrCl_2$ in a rac/meso ratio of 2/1 in 70% yield. (Grossman, R. B.; Doyle, R. A.; Buchwald, S. L. *Organometallics* 1991, 10, 1501). In general, these salt elimination procedures produce the desired rac ansa-metallocenes in 10%–30% yield after tedious separation and purification steps, and the separation of the rac from the meso products is not always possible.

Ansa-metallocenes can also be prepared by amine elimination reactions of ansa-bis-cyclopentadienes and metal amide complexes as disclosed in U.S. Pat. No. 5,597,935. An example is the reaction of $Zr(NMe_2)_4$ with 1,2-bis(3-indenyl)ethane $((EBI)H_2)$, shown below (Eq. 2). This reaction provides an efficient, high-yield synthesis of pure rac-$(EBI)Zr(NMe_2)_2$, which can easily be converted to rac-$(EBI)ZrCl_2$ and related derivatives.

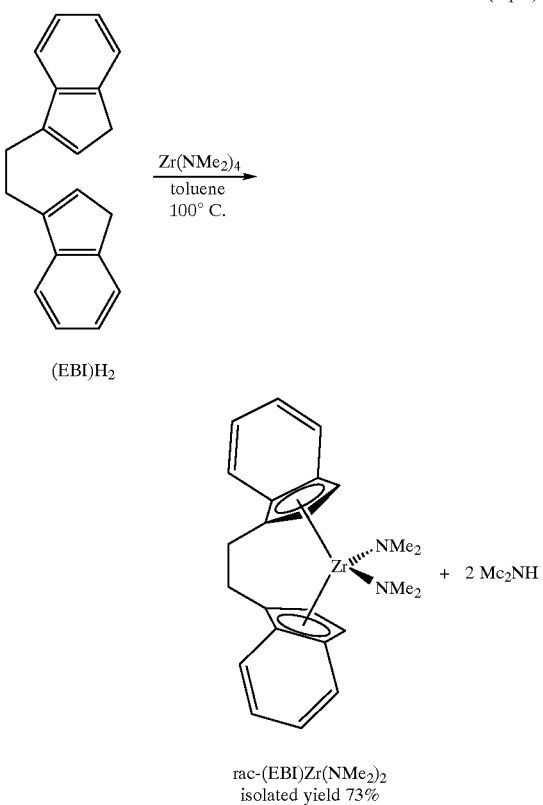

(EBI)H₂ rac-(EBI)Zr(NMe₂)₂
isolated yield 73%

However, this amine elimination reaction produces the noxious gaseous amine NMe₂H as a byproduct which must be removed and disposed of. Additionally, the amine elimination approach is less useful for the synthesis of Ti or Hf ansa-metallocenes (order of reactivity: Zr>Hf>Ti) and does not work well with crowded metal amides, or crowded or weakly acidic cyclopentadienes. For example (EBI)H₂ does not react with Ti(NMe₂)₄ in toluene at 100° C. (Diamond, G. M.; Jordan, R. F.; Petersen, J. L. *Organometallics* 1996, 15, 4030–4037). Also, the reaction of Hf(NMe₂)₄ with (1-indenyl)₂SiMe₂ proceeds only under vigorous conditions (neat, 32 h, 120° C.) to give rac-{(1-indenyl)₂SiMe₂}Hf (NMe₂)₂ in 20% isolated yield, and the rearrangement product Me₂Si(η⁵-1-indenyl)(η³-2-indenyl)HF(NMe₂)₂ is observed as a side product (Christopher, J. N.; Jordan, R. F.; Petersen, J. L.; Young, V. G. Jr. *Organometallics* 1997, 16, 3044–3050).

Kunicki et al. reported that the simple unlinked metallocene (C₅H₅)₂TiCl₂ can be prepared by the reaction of {(C₅H₅)₂Al(OⁱPr)}₂ with TiCl₄ (Kunicki, A.; Sadowdki, R.; Zachara, J. *J. Organometal. Chem.* 1996, 508, 249). Ansa-metallocene complexes are not discussed in the Kunicki reference.

There is, therefore, a need for a process which would produce ansa-metallocene complexes in high yield without the formation of noxious gaseous byproducts. Additionally, there is a need for a process which would produce rac ansa-metallocenes in high yield without contamination by the meso isomer, since the rac isomer is most useful in stereoselective catalysis. The present invention has as its primary objectives the fulfillment of these needs.

SUMMARY OF THE INVENTION

The process of preparing ansa-metallocene complexes in high yield by reacting a metal leaving group complex with an aluminum ansa-bis-cyclopentadienyl compound.

DETAILED DESCRIPTION OF THE INVENTION

In the present invention, ansa-metallocene complexes of general formula

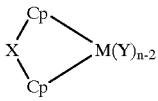

are prepared by reaction of a metal leaving group complex with an aluminum ansa-bis-cyclopentadienyl compound as illustrated in Eq. 3.

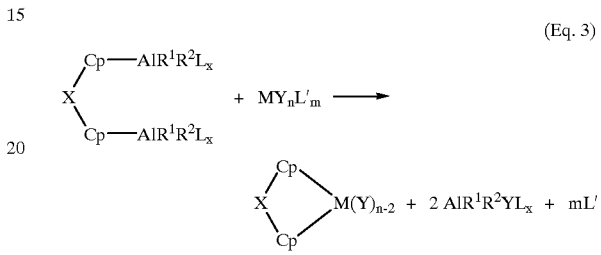

$R^1$ and $R^2$ represent hydrogen or hydrocarbyl radicals having from 1 to 20 carbon atoms, preferably from 1 to 4 carbon atoms. $R^1$ and $R^2$ may also be silyl radicals, alkoxide groups, aryloxide groups, amide groups or halogen. Al represents an aluminum atom. $R^1$ and $R^2$ may be the same, different or linked. Preferably $R^1$ and $R^2$ are methyl.

Cp independently in each occurrence is a cyclopentadienyl, indenyl, fluorenyl or related group that can π-bond to the metal, or a hydrocarbyl, alkyl, aryl, silyl, halo, halohydrocarbyl, hydrocarbylmetalloid, or halohydrocarbylmetalloid substituted derivative thereof. Cp may contain up to 150 nonhydrogen atoms.

X may be any bridging or ansa group that is used to link the Cp groups, including, for example, silylene (—SiH₂—) or substituted silylene, benzo (C₆H₄) or substituted benzo, methylene (—CH₂—) or substituted methylene, ethylene (—CH₂CH₂—), or substituted ethylene bridges.

L independently in each occurrence is a Lewis base. Preferably, L is selected from the group consisting of ethers, amines, pyridines and sulfides. L may be linked with $R^1$ and/or $R^2$. Preferably L is an ether.

M represents the metal used and is usually a Group 4 metal selected from the group consisting of titanium, zirconium and hafnium, but may also be a Group 3 (Sc,Y,La) or Group 5 (V,Nb,Ta) metal. Preferably it is a Group 4 metal, and most preferably it is zirconium or hafnium.

L' independently in each occurrence is a Lewis base. Preferably L' is selected from the group consisting of ethers, amines, pyridines and sulfides. Most preferably L' is an ether or a sulfide.

n is a whole number and is from 3 to 5. When M is a Group 4 metal "n" is 4, when M is a Group 3 metal "n" is 3, and when M is a Group 5 metal "n" is 5.

x is 0, 1, 2 or 3. Preferably x=1. m is 0, 1, or 2.

Y is a leaving group selected from the group consisting of amide (NR³R⁴), alkoxy (OR³), aryloxy, SR³, PR³R⁴, F, Cl, Br, I, OC(O)R³, or OS(O)₂R³, where $R^3$ and $R^4$ are each hydrogen, hydrocarbyl radicals of from $C_1$ to $C_{20}$ or silyl radicals and $R^3$ and $R^4$ may be the same or different or linked. The Y groups may be the same, different or linked (chelating). The Y and L' groups may also be linked. Preferably, Y is an amide group (NR³R⁴), and most preferably it is NMe₂.

The process of making each starting material for this reaction is known.

In particular, aluminum ansa-bis-cyclopentadienyl, indenyl and fluorenyl compounds can be prepared by the reaction of aluminum halide compounds with lithium ansa-bis-cyclopentadienyl indenyl, and fluorenyl reagents.

Metal amide complexes $M(NR^3R^4)_4$ can be prepared by reacting the corresponding metal tetrahalide complex such as zirconium tetrachloride with an appropriate lithium amide, see D. C. Bradley and I. M. Thomas, *Proc. Chem. Soc.*, 1959, 225; *J. Chem. Soc.* 1960, 3857.

The reaction between the aluminum ansa-bis-cyclopentadienyl compound and the metal leaving group compound can take place at any temperature from −80° C. to ambient, i.e., about 25° C. on up to 250° C., but is preferably within the range of 0° C. to 100° C. At 80° C. the reaction is typically complete in less than 24 hours.

The reaction desirably is conducted in the presence of a nonaqueous, nonalcoholic solvent that at least partially dissolves one of the reactants. Typical of such solvents are hydrocarbons such as benzene, toluene, nonane, m-xylene and hexane, simple ethers, chlorinated hydrocarbons such as chlorobenzene, tetrahydrofuran, etc.

It is believed that the metallocene complexes which are produced in Eq. 3 may, when activated by a suitable cocatalyst, be used as catalysts in many applications. Alternatively, the metallocene complexes which are produced in Eq. 3 may be converted to the more commonly used metallocene chloride or alkyl complexes by simple reactions.

For example, metallocene bis-amide complexes produced in Eq. 3 may be converted to metallocene dichloride complexes by reaction with $SiMe_3Cl$ and to metallocene dimethyl complexes by reaction with $AlMe_3$ as described in Diamond, G. M.; Jordan, R. F.; Petersen, J. L. *J. Am. Chem. Soc.* 1996, 118, 8024–8033.

Certain other modifications of this generalized reaction are apparent and come within the contemplated scope of the invention. For example, one may use enantiomerically enriched chiral metal starting materials ($MY_nl'_m$) to prepare enantiomerically enriched chiral ansa-metallocene derivatives directly. One may use an excess of the aluminum ansa-bis-cyclopentadienyl compound to increase the yield and the rate of formation of the ansa-metallocene product ($XCp_2MY_{n-2}$). In this regard, one may use from 1 to 100 equivalents of the aluminum ansa-bis-cyclopentadienyl compound per equivalent of $My_nL'_m$. Preferably, 1 to 1.3 equivalents of the aluminum ansa-bis-cyclopentadienyl compound are used per equivalent of $MY_nL'_m$.

Each of these, as well as other variations that readily come to the mind of one of ordinary skill in the art after knowing the basic reaction, fall within the contemplated scope of the invention.

The following examples are offered to further illustrate but not limit the process of the present invention.

EXAMPLE 1
{AlMe2(THF)-indenyl}$_2$SiMe$_2$

A solution of $AlMe_2Cl$ (2.13 g, 23.0 mmol) in hexanes (10 ml) was diluted with Et2O (50 mL). The colorless solution was slowly added (10 min) to solid Li$_2$SBI (3.48 g, 11.5 mmol) via cannula. The yellow slurry was stirred overnight at 23° C. The volatiles were removed under vacuum affording a yellow-orange residue. The residue was taken up in hexanes (50 mL), and the mixture was filtered to afford a pale yellow filtrate and a white solid (LiCl; 0.95 g; 0.97 g expected). The filtrate volume was reduced to ca. 10 ml under vacuum, THF (10 ml) was added, and the solution was stirred for 5 min. The volatiles were removed under vacuum. The red orange residue was taken up in hexanes (50 mL) and stirred for 3 h at 23° C., which resulted in the precipitation of an off-white solid. The mixture was filtered, yielding a cream-colored solid which was dried under vacuum (3.12 g). The filtrate was concentrated to ca. 15 ml, cooled to −78° C. for 30 min, and filtered cold to yield a second crop of white solid (0.28 g), which was combined with the first crop. Total yield 3.40 g (54%). The $^1H$ NMR spectrum ($C_6D_6$) established that this product was a 1.2/1 mixture of rac and meso {AlMe$_2$(THF)-indenyl}$_2$SiMe$_2$. Anal. Calcd for $C_{32}H_{46}Al_2O_2Si$: C, 70.55; H, 8.51; Al, 9.90, Si, 5.15. Found: C, 69.65; H, 8.26; Al, 9.76, Si, 4.20. $^1H$ NMR ($C_6D_6$): d 7.87 (d, J=6.3, 4H, indenyl), 7.60 (d, J=6.3, 4H, indenyl), 7.29 (d, 2H, H2 meso), 7.15 (overlapped with solvent signal), 7.08 (br, 2H, H2 rac), 5.69 (br, 4H, E3 rac and meso), 2.59 (br, 16H, THF), 0.96 (s, 3H, SiMe$_2$ meso), 0.88(s, 6H, SiMe$_2$ rac), 0.64 (s, 16H, THF), 0.53 (s, 3H, SiMe$_2$ meso), −0.44 (s, 12H, AlMe$_2$ meso), −0.47 (s, 12H, AlMe$_2$ rac). $^1H$ NMR (THF-d$_8$, fast solvent exchange ): d 7.52 (m, 4H, indenyl), 7.37 (m, 4H, indenyl), 6.90 (m, 10H, indenyl), 6.78 (br, 2H, H2 rac), 5.36 (br, 4H, H3 rac and meso). 0.59 (s, 3H, SiMe$_2$ meso), 0.51 (s, 6H, SiMe$_2$ rac), 0.22 (s, 3H, SiMe$_2$ meso), −0.91 (s, 12H, AlMe2 rac), −0.94 (s, 12H, AlMe$_2$ meso).

EXAMPLE 2
{1-AlMe$_2$(Et$_2$O)-2-Me-4,5-benz-1-indenyl}$_2$SiMe$_2$

A solution of $AlMe_2Cl$ (1.46 g, 15.8 mmol) in hexanes (4 mL) was diluted with Et$_2$O (100 mL). The colorless solution was slowly added to yellow solid Li$_2$[(2-Me-4,5-benz-1-indenyl)$_2$SiMe$_2$] (4.00 g, 7.82 mmol) via cannula. The colorless slurry was stirred at 23° C. for 2 h. The volatiles were removed under vacuum affording a colorless solid which was dried overnight. Toluene (90 mL) was added and the colorless slurry was stirred for 10 min and filtered to afford a pale yellow filtrate and a colorless solid (LiCl). The LiCl was washed with toluene (40 mL) and the wash was combined with the filtrate. The volatiles were removed from the filtrate under vacuum affording a colorless solid. Hexanes (75 mL) were added to the solid and the resulting colorless slurry was stirred for 30 min. cooled to 0° C. for 1 h and filtered to yield a colorless solid and a yellow filtrate. The solid was dried under vacuum (3.76 g, 70%). The $^1H$ NMR spectrum in $C_6D_6$ at 23° C. established that the solid was a 2/1 mixture of rac and meso-{1-AlMe$_2$(Et$_2$O)-2-Me-4,5-benz-1-indenyl}2SiMe$_2$. This material was recrystallized from toluene/hexanes (3:2 by volume) at 23° C. by slow evaporation yielding pure rac-{AlMe$_2$(Et$_2$O)-2-Me-4,5-benz-1-indenyl}$_2$SiMe$_2$ as colorless blocks whose molecular structure was confirmed by X-ray crystallography. Data for rac-{AlMe$_2$(Et$_2$O)-2-Me-4,5-benz-1-indenyl}$_2$SiMe$_2$: Anal Calcd. for $C_{42}H_{58}Al_2O_2Si$: C, 74.66; H. 8.63, Al, 7.96; Si, 4.14. Found: C, 72.21; H, 8.38; Al, 7.96; Si, 3.54. 1H NMR ($C_6D_6$): d 8.15 (d, J=7.2, 2H), 8.11 (d, J=7.2, 2H), 7.91 (d, J=7.2, 2H), 7.54 (d, J=7.2, 2H), 7.40 (t, J=7.2, 2H), 7.34 (t, J=7.2, 2H), 6.46 (s, 2H, H3 on indenyl C$_5$ ring), 2.47 (br, 8H, Et$_2$O), 1.83 (s, 6H, 2-Me), 1.30 (s, 6H, SiMe$_2$), 0.00 (br, 12H, Et$_2$O), −0.28 & −0.40 (two br s, 12H, AlMe$_2$). $^1H$ NMR (toluene-d$_8$, −20° C.): d 8.17 (d, J=3.6, 2H), 8.15 (d, J=3.6, 2H), 7.91 (d, J=7.2, 2H), 7.54 (d, J=7.2, 2H), 7.45 (m, 2H), 7.37 (m, 2H), 6.64 (s, 2H, H3 on indenyl C$_5$ ring), 2.36 (q, J=7.2, 4H, Et$_2$O), 2.20 (q, J=7.2, 4H, Et$_2$O), 1.66 (s, 6H, 2-Me), 1.39 (s, 6H, SiMe$_2$), −0.08 (t, J=7.2, 12H, Et$_2$O), −0.24 (s, 6H, AlMe$_2$), −0.44 (s, 6H, AlMe$_2$). $^{13}C\{^1H\}$ NMR ($C_6D_6$): d 151.0 (C), 144.1 (C), 139.2 (C), 130.7 (C), 128.6 (2 CH), 128.4 (C), 124.6 (CH), 124.5 (CH), 124.1(CH), 124.0 (CH), 119.9 (CH), 109.9 (br, indenyl Cl), 67.2 (Et$_2$O), 18.3 (2-Me), 12.8 (Et$_2$O), 5.1

(SiMe$_2$), −6.5 (br, AlMe$_2$). Data for meso-{AlMe$_2$(Et$_2$O)-2-Me-4,5-benz-1-indenyl}$_2$SiMe$_2$ (from rac/meso mixture): $^1$H NMR (C$_6$D$_6$, 60° C.): d 7.98 (d, J=7.2, 2H), 7.72 (d, J=7.2, 2H), 7.64 (d, J=7.2, 2H), 7.30 (m, overlapped with rac resonance), 6.15 (s, 2H, H3 on indenyl C$_5$ ring), 2.56 (q, J=7.2, Et$_2$O, overlapped with rac resonance), 2.49 (s, 6H, 2-Me), 1.08 (s, 3H, SiMe$_2$), 0.97 (s, 3H, SiMe$_2$), 0.15 (t, J=7.2, Et$_2$O, overlapped with rac resonance), −0.47 (s, 12H, AlMe). $^{13}$C {$^1$H}NMR (C$_6$D$_6$, 60° C.): d 151.8 (C), 144.2 (C), 139.6 (C), 130.7(C), 128.6 (C), 124.5 (CH), 124.1 (CH), 122.9 (CH), 124.5 (CH), 124.1 (CH), 120.1 (CH), 100.4 (indenyl Cl), 67.5 (Et$_2$O, overlapped with rac resonance), 19.5 (2-Me), 12.9 (Et$_2$O, overlapped with rac resonance), 4.4 (SiMe$_2$), 4.1 (SiMe$_2$), −7.0 (br, Al—Me). One aromatic resonance is obscured.

EXAMPLE 3

Rac-{1-AlMe$_2$(THF)-2-Me-4-Ph-1-indenyl}$_2$SiMe$_2$

A solution of AlMe$_2$Cl (0.68 g, 7.3 mmol) in hexanes (4.0 mL) was diluted with Et$_2$O (60 mL). The colorless solution was slowly added to yellow solid Li$_2$[(2-Me-4-Ph-1-indenyl)$_2$SiMe$_2$] (2.00 g, 3.65 mmol) via cannula. The pale yellow slurry was stirred at 23° C. for 2 h. The volatiles were removed under vacuum affording a pale brown foamy solid which was dried overnight. Toluene (40 mL) was added and the resulting slurry was filtered to afford a pale yellow filtrate and a colorless solid (LiCl). The volatiles were removed from the filtrate under vacuum affording a pale brown foamy solid. Hexanes (50 mL) were added to the solid and the resulting slurry was stirred for 30 min, concentrated to 10 ml and filtered to yield a colorless solid and a yellow filtrate. THF (10 mL) was added to the yellow filtrate and the mixture was stirred for 5 min. The volatiles were removed under vacuum to give a colorless solid. Hexanes (70 mL) were added and the mixture was stirred overnight and filtered yielding a colorless solid which was washed with hexanes and dried under vacuum (1.63 g, 61.7%). $^1$H NMR analysis (C$_6$D$_6$, 23° C) established that the solid was pure rac-{1-AlMe$_2$(THF)-2-Me-4-Ph-1-indenyl}$_2$SiMe$_2$. Anal Calcd. for C$_{46}$H$_{58}$Al$_2$O$_2$Si: C, 76.19; H, 8.07, Al, 7.44; Si, 4.14. Found: C, 75.21; H, 8.19; Al, 7.41; Si, 4.53. $^1$H NMR (C$_6$D$_6$): d 7.97 (d, J=7.2, 2H), 7.75 (d, J=7.2, 4H), 7.42 (t, J=7.2, 4H), 7.24 (m, 6H), 6.50 (s, 2H, H3 of C$_5$ indenyl ring), 2.65 (br, 4H, THF), 2.26 (br, 4H, THF), 1.72 (s, 6H, 2-Me), 1.35 (s, 6H, SiMe$_2$), 0.54 (br, 8H, THF), −0.26 & −0.40 (two br s, 12H, AlMe$_2$). $^1$H NMR (toluene-d$_8$, −30° C.): d 8.01 (d, J=7.2, 2H), 7.80 (d, J=7.2, 4H), 7.46 (t, J=7.2, 4H), 7.27 (m, 6H), 6.58 (s, 2H, H3 of C$_5$ indenyl ring), 2.57 (br, 4H, THF), 2.06 (br,THF, partially obscured by solvent), 1.67 (s, 6H, 2-Me), 1.38 (s, 6H, SiMe$_2$), 0.45 (br, 8H, THF), −0.17 (s, 6H, AlMe$_2$), −0.44 (s, 6H, AlMe$_2$). $^{13}$C{$^1$H} NMR (C$_6$D$_6$): d 152.2 (C), 148.9 (C), 144.3 (C), 142.1 (C), 133.1 (C), 129.6 (2 CH), 129.0 (CH), 126.6 (CH), 123.6 (CH), 121.9 (CH), 120.5 (CH), 119.2 (br, indenyl Cl), 71.9 (THF), 24.4 (THF), 18.1 (2-Me), 5.6 (SiMe$_2$), −6.8 (br, AlMe$_2$).

EXAMPLE 4

1,2-{3-AlMe$_2$(THF)-1-indenyl}$_2$-ethane

A solution of AlMe$_2$Cl (3.86 g, 41.7 mmol) in hexanes (4 mL) was diluted with Et$_2$O (60 mL) at 10° C. The colorless solution was slowly added to pale yellow solid Li$_2$[1,2-(indenyl)$_2$-ethane] (5.39 g, 19.8 mmol) via cannula at 0° C. The yellow slurry was stirred at 23° C. for 2 h. The reaction mixture was filtered to afford a pale orange filtrate and a white solid (LiCl). The filtrate was concentrated to ca. 15 mL under vacuum, THF (8 mL) was added at 0° C. and the solution was stirred for 5 min at 0° C. The volatiles were removed under vacuum affording an orange oily residue. The residue was taken up in hexanes (40 mL) and stirred overnight. Toluene (20 mL) was added and the mixture was stirred for 3 h. The resulting slurry was filtered yielding a cream-colored solid and a pale yellow filtrate. Hexanes (40 mL) were added to the solid and the mixture was stirred for 2 h and filtered to yield a off-white solid and a pale yellow filtrate. The solid was dried under vacuum (5.62 g). The filtrates were combined and the volatiles were removed under vacuum. The residue was taken up in hexanes (20 mL), stirred for 10 h and filtered to yield a white crystalline powder (0.12 g), which was combined with the first crop. Total yield 5.74 g (53.6%). The $^1$H NMR spectrum (C$_6$D$_6$) established that this product is a single isomer of 1,2-{3-AlMe$_2$(THF)-1-indenyl}$_2$-C$_2$H$_4$. The solid was recrystallized from toluene at −20° C. affording a white crystalline solid. Anal Calcd. for C$_{32}$H$_{44}$Al$_2$O$_2$: C, 74.66; H, 8.63; Al, 10.48. Found: C, 73.65; H, 8.28; Al, 10.63. $^1$H NMR (C$_6$D$_6$): d 7.73 (d, J=7.2, 2H, H4 or H7), 7. 70 (d, J=7.2, 2H, H4 or H7), 7.29 (m, 4H, H5 and H6), 7.00 (s, 2H, H2), 3.99 (s, 2H, H1), 3.29 (m, 4H, C$_2$H$_4$), 2.78 (br s, 8H, THF), 0.70 (br s, 8H, THF), −0.46 (br, 12H, AlMe). $^1$H NMR (toluene-d$_8$, −90° C.): d 7.83 (br S, 2H), 7.66 (br s, 2H), 7.35 (br s, 4H), 7.08 (br s, 2H, H2), 4.14 (s, 2H, H1), 3.28 (m, 4H, C$_2$H$_4$), 2.57 (br s, 4H, THF), 1.92 (br s, 4H, THF), 0.44 (br s, 8 H, THF), −0.21 (br, 12H, AlMe). $^{13}$C{$^1$H} NMR (C$_6$D$_6$): d 147.9 (C), 141.9 (C), 132.5 (C), 129.0 (br, C3), 122.1 (CH), 121.8 (CH), 121.5 (CH), 118.6 (CH), 71.3 (THF), 52.4 (C1), 28.4 (C$_2$H$_4$), 24.7 (THF), −9.5 (br AlMe).

EXAMPLE 5

{(1-indenyl)$_2$SiMe$_2$}Zr(NMe$_2$)$_2$

An NMR tube was charged with {AlMe$_2$(THF)-indenyl}$_2$SiMe$_2$ (rac/meso=1/1, 0.16 g, 0.29 mmol), Zr(NMe$_2$)$_4$ (0.060 g, 0.22 mmol), and C$_6$D$_6$ (0.5 mL). The tube was maintained at 23° C. and monitored periodically by $^1$H NMR. The pale yellow solution became dark orange. After 50 h at 23° C, the $^1$H NMR spectrum established that the starting materials were completely consumed and {(1-indenyl)$_2$SiMe$_2$}Zr(NMe$_2$)$_2$ (90% based on total NMe$_2$, rac/meso 4/1) and Al2Me$_4$(m-NMe$_2$)$_2$ (100% based on total NMe$_2$) were present. The THF resonances had shifted to positions characteristic of free THF (d 3.60, 1.42). The $^1$H NMR data for the products are consistent with literature data.

EXAMPLE 6

Rac-{(1-indenyl)$_2$SiMe$_2$}Hf(NMe$_2$)$_2$

A solution of Hf(NMe$_2$)$_4$ (1.24 g, 3.49 mmol) in benzene (35 mL) was added to solid {AlMe$_2$(THF)-indenyl}$_2$SiMe$_2$ (1, 2.50 g, 4.59 mmol). The pale yellow solution was heated to 76° C. and stirred for 24 h. The volatiles were removed under vacuum affording an orange solid. The solid was extracted with mixture of toluene (15 mL) and hexanes (110 mL). The extract was filtered, concentrated to ca. 30 mL, and cooled to −38° C. After 2 h, pale-orange needles were collected by filtration and dried under vacuum (1.19 g, 61% based on Hf(NMe$_2$)$_4$). The $^1$H NMR spectrum established that this product is pure rac-{(1-indenyl)$_2$SiMe$_2$}Hf(NMe$_2$)$_2$.

EXAMPLE 7

{1,2-(indenyl)$_2$C$_2$H$_4$}Zr(NMe$_2$)$_2$

An NMR tube was charged with 1,2-{3-AlMe$_2$(THF)-1-indenyl}$_2$C$_2$H$_4$ (0.086 g, 0.16 mmol), Zr(NMe$_2$)$_4$ (0.034 g, 0.13 mmol), and C$_6$D$_6$ (~0.5 mL). The tube was heated to 80° C. and monitored by $^1$H NMR. The pale yellow solution became dark orange. After 19 h at 80° C., the $^1$H NMR spectrum established that the starting materials were completely consumed and {1,2-(indenyl)$_2$C$_2$H$_4$}Zr(NMe$_2$)$_2$ (70% based on total NMe$_2$, rac/meso=7.3/1) and Al2Me$_4$ (m-NMe$_2$)$_2$ (100% based on total NMe$_2$) were present. The THF resonances had shifted to positions characteristic of free THF. The $^1$H NMR data for the reaction products are consistent with literature data.

EXAMPLE 8
{1,2-(indenyl)$_2$C$_2$H$_4$}Hf(NMe$_2$)$_2$

An NMR tube was charged with {1,2-{3-AlMe$_2$(THF)-1-indenyl}$_2$C$_2$H$_4$ (0.12 g, 0.24 mmol), Hf(NMe$_2$)$_4$ (0.064 g, 0.18 mmol), and C$_6$D$_6$ (0.5 mL). The tube was heated to 80° C. and monitored by $^1$H NMR. The pale yellow solution became dark orange. After 27 h at 80° C., the $^1$H NMR spectrum established that the starting materials were completely consumed and {1,2-(indenyl)$_2$C$_2$H$_4$}Hf(NMe$_2$)$_2$ (80% based on total NMe$_2$, rac/meso=7/1) and Al$_2$Me$_4$(m-NMe$_2$)$_2$ (100% based on total NMe$_2$) were present. The THF resonances had shifted to positions characteristic of free THF. $^1$H NMR data for the reaction products are consistent with literature data.

EXAMPLE 9
Zr(NMePh)$_4$

ZrCl$_4$ (2.20 g, 9.44 mmol) was added to a slurry of LiNMePh (4.26 g, 37.7 mmol) in toluene (150 mL) in several portions over 2 h. The mixture was stirred at 23° C. for 25 h. The volatiles were removed under vacuum and the residue was extracted with hexanes (50 mL) and benzene (2×70mL). The extracts were combined and the volatiles were removed under vacuum yielding Zr(NMePh)$_4$ as a pale yellow powder (2.18 g, 45% yield). Anal. Calcd for C$_{28}$H$_{32}$N$_4$Zr: C, 65.19; H, 6.27; N, 10.86. Found: C, 64.82; H, 6.40; N, 10.47. $^1$H NMR (C$_6$D$_6$): d 7.11 (t, J=7.2, 2H, Ph), 6.86 (d, J=7.2, 2H, Ph), 6.77 (t, J=7.2, 1H, Ph), 2.97 (s, 3H, NMe). $^{13}$C{$^1$H} NMR (C$_6$D$_6$): d 151.9, 129.9, 120.6, 116.3, 32.8.

EXAMPLE 10
{(2-Me-4,5-benz-1-indenyl)$_2$SiMe$_2$}Zr(NMePh)$_2$

An NMR tube was charged with {1-AlMe$_2$(Et$_2$O)-2-Me-4,5-benz-1-indenyl}$_2$SiMe$_2$ (0.040 g, 0.058 mmol), Zr(NMePh)$_4$ (0.030 g, 0.058 mmol), hexamethylbenzene (0.005 g, 0.031 mmol, internal standard) and C$_6$D$_6$ (0.6 mL). The tube was maintained at 75° C. and monitored periodically by $^1$H NMR. The yellow solution turned dark red. After 46 h at 75° C., $^1$H NMR analysis indicated that {(2-Me-4,5-benz-1-indenyl)$_2$SiMe$_2$}Zr(NMePh)$_2$ was formed in 60% yield (mole % vs internal standard) in a 5:1 rac/meso ratio, together with {(2-Me-4,5-benz-1-indenyl )$_2$SiMe$_2$}{Zr (NMePh)$_3$}$_2$ (13% vs internal standard).

EXAMPLE 11
Rac-{(2-Me-4,5-benz-1-indenyl)$_2$SiMe$_2$}Zr(NMePh)$_2$

A solution of Zr(NMePh)$_4$ (0.870 g, 1.68 mmol) and {1-AlMe$_2$(Et$_2$O)-2-Me-4,5-benz-1-indenyl}$_2$SiMe$_2$ (1.50 g, 2.18 mmol) in toluene (60 ad) was stirred and heated at 75° C. for 34 h. The mixture was cooled to 23° C. and the volatiles were removed under vacuum. The solid was triturated with hexanes (60 mL), washed further with hexanes (3×30 mL) and dried under vacuum for 24 h at 23° C. The $^1$H NMR spectrum indicated that this product is pure rac-{(2-Me-4,5-benz-1-indenyl)$_2$SiMe$_2$}Zr(NMePh)$_2$ (235 mg, 20%). $^1$H NMR (C$_6$D$_6$): d 8.10 (dd, J=7.2, 3, 2H, indenyl), 7.79 (d, J=7.2, 2H, indenyl), 7.55 (m, 2H1, indenyl), 7.35 (d, J=10.8, 2H, indenyl), 7.27–7.22 (m, 8H, indenyl+Ph), 6.96 (tt, J=7.2, 1, 2H, Ph), 6.86 (d, J=7.2, 4H, Ph), 6.74 (s, 2H, H3), 2.26 (s, 6H), 2.05 (s, 6H), 0.87 (s, 6H, SiMe$_2$). $^{13}$C{$^1$H} NMR (C$_6$D$_6$): d 162.4, 130.7, 129.2, 128.8, 126.6, 126.3, 126.0, 125.9, 125.3, 125.0, 123.7, 122.3, 117.4, 98.5, 49.0 (NMePh), 18.3 (2-Me), 1.8 (SiMe$_2$). A sample was recrystallized from toluene. Anal. Calcd for C$_{44}$H$_{42}$N$_2$SiZr.C$_7$H$_8$: C, 75.59; H, 6.23; N, 3.46. Found: C, 75.67; H, 6.45; N, 3.30.

EXAMPLE 12
{(2-Me-4-Ph-1-indenyl)$_2$SiMe$_2$}ZrCl$_2$

An NMR tube was charged with rac-{AlMe$_2$(THF)-2-Me-4-Ph-1-indenyl)}$_2$SiMe$_2$ (0.250 g, 0.345 mmol) and ZrCl$_4$ (0.062 g, 0.266 mmol) and CD$_2$Cl$_2$ (ca. 0.6 mL) was added. An orange solution formed immediately. The tube was maintained at 23° C. for 70 mins, and an orange solid formed. The solid was collected by filtration, washed with hexane and dried under vacuum to afford an orange solid (0.133 g, 84%). The $^1$H NMR spectrum established that this material was {(2-Me-4-Ph-1-indenyl)$_2$SiMe$_2$}ZrCl$_2$ with a 1/1 rac/meso ratio.

EXAMPLE 13
{(2-Me-4,5-benz-1-indenyl)$_2$SiMe$_2$}ZrCl$_2$

A solution of rac-{1-AlMe$_2$(Et$_2$O)-2-Me-4,5-benz-1-indenyl)}$_2$SiMe$_2$ (0.055 g, 0.091 mmol) in 0.6 mL C$_6$D$_6$ was added to ZrCl$_4$(SMe$_2$)$_2$ (0.029 g, 0.081 mmol). The mixture was stirred for 6 h at 23° C., affording a yellow slurry. The supernatant was removed and the yellow solid was dried under vacuum. The $^1$H NMR spectrum established that this material was pure {(2-methyl-4,5-benz-1-indenyl)$_2$ SiMe$_2$}ZrCl$_2$ with a 1.2/1 rac/meso ratio and the yield was quantitative.

What is claimed is:

1. A process of synthesizing in high yield ansa-metallocene complexes of the formula:

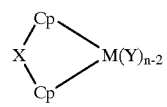

wherein Cp independently and in each occurrence is cyclopentadienyl, indenyl, fluorenyl, or a related group that can p-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group that links the Cp groups, M is a metal selected from the group consisting of Group 3, 4 and 5 metals, Y is a leaving group wherein each Y moiety may be the same or different or linked, and n is from 3 to 5, said process comprising:

reacting an aluminum ansa-bis-cyclopentadienyl compound of the formula:

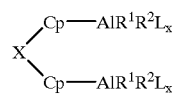

wherein Cp is as defined above, X is as defined above, Al is aluminum, R$^1$ and R$^2$ are hydrogen, hydrocarbyl radicals of from C$_1$ to C$_{20}$, alkoxide groups, aryloxide groups, amide groups or halogen and R$^1$ and R$^2$ may be the same, different or linked, L independently in each occurrence a Lewis base and x is 0, 1, 2 or 3, with a metal leaving group complex of the formula:

$MY_nL'_m$ wherein M is as defined above, Y is as defined above, n is as defined above, L' independently in each occurrence a Lewis base, m is 0, 1, or 2, and two or more Y and L' groups may be linked, to provide a high yield of ansa-metallocene complex.

2. The process of claim 1 wherein the metal leaving group complex $MY_nL'_m$ is a metal amide $M(NR^3R^4)_4$ of a group 4 metal and $R^3$ and $R^4$ are each hydrogen, hydrocarbyl radicals of from $C_1$ to $C_{20}$ or silyl radicals and $R^3$ and $R^4$ may be the same or different or linked.

3. The process of claim 1 wherein M is a Group 4 metal selected from the group consisting of zirconium, titanium and hafnium.

4. The process of claim 3 wherein the metal is zirconium.

5. The process of claim 3 wherein the metal is hafnium.

6. The process of claim 1 wherein Y is selected from the group consisting of $NR^3R^4$, $R^3$, $OR^3$, $SR^3$, $PR^3R^4$, F, Cl, Br, I, $OC(O)R^3$, $OS(O)_2R^3$ and may be the same or different or linked and $R^3$ and $R^4$ are each hydrogen; or hydrocarbyl radicals of from $C_1$ to $C_{20}$ or silyl radicals, and $R^3$ and $R^4$ may be the same, different or linked.

7. The process of claim 6 wherein Y is a $NR^3R^4$ group.

8. The process of claim 7 wherein $R^3$ and $R^4$ are independently $C_1$ to $C_4$ alkyl, and may be the same, different or linked.

9. The process of claim 8 wherein $R^3$ and $R^4$ are methyl.

10. The process of claim 1 wherein the metal leaving group complex $MY_nL'_m$ is $ZrCl_4(SMe_2)_2$.

11. The process of claim 1 wherein said process is conducted at a temperature ranging from $-80°$ C. to $250°$ C.

12. The process of claim 11 wherein said process is conducted at a temperature ranging from $0°$ C. to $250°$ C.

13. The process of claim 12 wherein the temperature is from $23°$ C. to $100°$ C.

14. The process of claim 1 wherein the reaction is conducted in the presence of a nonaqueous, non-alcoholic organic solvent.

15. The process of claim 14 wherein the solvent is selected from the group consisting of hydrocarbons, toluene, ethers, chlorinated hydrocarbons and tetrahydrofuran.

16. The process of claim 1 where X is ethylene and Cp is indenyl.

17. The process of claim 1 wherein X is methylene or substituted methylene.

18. The process of claim 1 wherein X is silylene or substituted silylene.

19. The process of claim 1 wherein an excess of the aluminum ansa-bis-cyclopentadienyl compound is used.

20. The process of claim 1 wherein X is $SiMe_2$.

21. A process of synthesizing in high yield ansa-metallocene complexes of the formula:

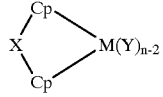

wherein Cp independently and in each occurrence is cyclopentadienyl, indenyl, fluorenyl, or a related group that can p-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group that links the Cp groups, M is a metal selected from the group consisting of Group 3, 4 and 5 metals, Y is a leaving group wherein each Y moiety may be the same or different or linked, and n is from 3 to 5, said process comprising:

reacting an aluminum ansa-bis-cyclopentadienyl compound of the formula:

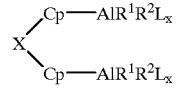

wherein Cp is as defined above, X is as defined above, Al is aluminum, $R^1$ and $R^2$ are hydrogen, hydrocarbyl radicals of from $C_1$ to $C_{20}$, alkoxide groups, aryloxide groups, amide groups or halogen and $R^1$ and $R^2$ may be the same, different or linked, L independently in each occurrence a Lewis base and x is 0, 1, 2 or 3, with a metal leaving group complex of the formula:

$MY_nL'_m$ wherein M is as defined above, Y is as defined above, L' independently in each occurrence a Lewis base, m is 0, 1, or 2, and two or more Y and L' groups may be linked, to provide a high yield of ansa-metallocene complex and isolating the metallocene complex from the reaction mixture.

22. The process of claim 21 wherein the metal leaving group complex $MY_nL'_m$ is metal amide $M(NR^3R^4)_4$ of a group 4 metal and $R^3$ and $R^4$ are each hydrogen, hydrocarbyl radicals of from $C_1$ to $C_{20}$ or silyl radicals and $R^3$ and $R^4$ may be the same or different or linked.

23. The process of claim 22 wherein the metal is zirconium and n is 4.

24. The process of claim 22 wherein the metal is hafnium and n is 4.

25. The process of claim 22 wherein $R^3$ and $R^4$ are both methyl.

26. The process of claim 22 wherein X is an ethylene moiety and Cp is indenyl.

27. The process of claim 22 wherein X is silylene or substituted silylene.

28. The process of claim 27 wherein X is $SiMe_2$.

29. The process of claim 22 wherein an excess of the aluminum ansa-bis-cyclopentadienyl compound is used.

30. A process of synthesizing in high yield ansa-metallocene complexes of the formula:

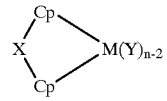

wherein Cp independently and in each occurrence is cyclopentadienyl, indenyl, fluorenyl, or a related group that can p-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group that links the Cp groups, M is a metal selected from the group consisting of Group 3, 4 and 5 metals, Y is a leaving group wherein each Y moiety may be the same or different or linked, and n is from 3 to 5, said process comprising:

reacting an aluminum ansa-bis-cyclopentadienyl compound of the formula:

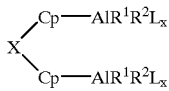

wherein Cp is as defined above, X is as defined above, Al is aluminum, $R^1$ and $R^2$ are hydrogen, hydrocarbyl radicals of from $C_1$ to $C_{20}$, alkoxide groups, aryloxide groups, amide groups or halogen and $R^1$ and $R^2$ may be the same, different or linked, L independently in each occurrence a Lewis base and x is 0, 1, 2 or 3, with a metal leaving group complex of the formula:

wherein M is as defined above, Y is as defined above, L' independently in each occurrence a Lewis base, m is 0, 1, or 2, and two or more Y and L' groups may be linked, to provide a high yield of rac ansa-metallocene complex.

31. The process of claim 30 wherein the metal leaving group complex $MY_nL'_m$ is metal amide $M(NR^3R^4)_4$ of a group 4 metal and $R^3$ and $R^4$ are each hydrogen, hydrocarbyl radicals of from $C_1$ to $C_{20}$ or silyl radicals and $R^3$ and $R^4$ may be the same or different or linked.

32. The process of claim 31 which includes as an additional step isolating the rac ansa-metallocene complex.

33. The process of claim 31 wherein X is ethylene and Cp is indenyl.

34. The process of claim 7 which includes a step of converting the ansa-metallocene amide complex to an ansa-metallocene chloride complex $XC_{p2}MCl_{n-2}$, an ansa-metallocene alkyl complex $XC_{p2}M(R)_{n-2}$ or other $XC_{p2}M(Y)_{n-2}$ derivatives.

35. The process of claim 31 wherein X is silylene or substituted silylene.

36. The process of claim 1 wherein an enantiomerically enriched chiral metal leaving group complex, $My_nL'_m$ is used to prepare an enantiomerically enriched chiral ansa-metallocene product.

37. A process of synthesizing in high yield ansa-metallocene complexes of the formula:

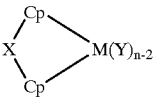

wherein Cp independently and in each occurrence is cyclopentadienyl, indenyl, fluorenyl, or a related group that can p-bond to the metal, or a hydrocarbyl, alkyl, aryl, silyl, halo, halohydrocarbyl, hydrocarbylmetalloid, or halohydrocarbylmetalloid substituted derivative of said cyclopentadienyl, indenyl, fluorenyl or related group, X is a bridging group that links the Cp groups, M is a metal selected from the group consisting of Group 3, 4 and 5 metals, Y is a leaving group wherein each Y moiety may be the same or different or linked, and n is from 3 to 5, said process comprising:

reacting an aluminum ansa-bis-cyclopentadienyl compound of the formula:

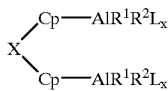

wherein Cp is as defined above, X is as defined above, Al is aluminum, $R^1$ and $R^2$ are hydrogen, hydrocarbyl radicals of from $C_1$ to $C_{20}$, alkoxide groups, aryloxide groups, amide groups or halogen and $R^1$ and $R^2$ may be the same, different or linked, L independently in each occurrence a Lewis base and x is 0, 1, 2 or 3, with a metal leaving group complex of the formula:

wherein M is as defined above, Y is as defined above, L' independently in each occurrence a Lewis base, m is 0, 1, or 2, and two or more Y and L' groups may be linked, to provide a high yield of rac ansa-metallocene complex and isolating the rac ansa-metallocene complex from the reaction mixture.

38. The process of claim 1 wherein $R^1$ and $R^2$ are methyl.

39. The process of claim 38 wherein L is an ether and x=1.

* * * * *